US006949240B2

(12) United States Patent
Sagel et al.

(10) Patent No.: US 6,949,240 B2
(45) Date of Patent: Sep. 27, 2005

(54) TOOTH WHITENING PRODUCTS

(75) Inventors: Paul Albert Sagel, Mason, OH (US); Robert Woodrow Gerlach, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 277 days.

(21) Appl. No.: 10/154,020

(22) Filed: May 23, 2002

(65) Prior Publication Data

US 2003/0219389 A1 Nov. 27, 2003

(51) Int. Cl.$^7$ .............................. A61K 7/16; A61K 7/18; A61K 7/20
(52) U.S. Cl. .................... 424/53; 424/401; 424/443; 433/80; 433/89; 433/136; 433/137; 433/138; 433/141; 433/146; 433/215; 433/216; 433/228.1
(58) Field of Search .................... 424/53, 401, 443; 433/80, 89, 136, 137, 138, 141, 146, 215, 216, 228.1

(56) References Cited

U.S. PATENT DOCUMENTS

| 2,835,628 A | 5/1958 | Saffir |
| 3,070,102 A | 12/1962 | MacDonald |
| 3,625,215 A | 12/1971 | Quisling |

(Continued)

FOREIGN PATENT DOCUMENTS

| CA | 1209761 | 8/1986 |
| CA | 2078960 | 10/1993 |
| CA | 2095445 | 7/1995 |
| CA | 2000040 | 10/1995 |
| CA | 2162536 | 5/1996 |
| CA | 2162812 | 5/1996 |
| CA | 2162885 | 5/1996 |
| DE | 1104116 | 4/1961 |
| DE | 2330869 | 1/1975 |
| EP | 0 063 604 | 4/1982 |
| EP | 0 200 508 | 12/1986 |
| EP | 0 252 459 | 1/1988 |
| EP | 0 381 194 | 8/1990 |
| EP | 0569797 A2 | 11/1993 |
| EP | 0636378 A1 | 2/1995 |
| EP | 0763358 | 9/1996 |
| FR | 2637 175 A | 4/1990 |
| FR | 2701397 A1 | 8/1994 |
| GB | 1142325 | 2/1969 |
| GB | 1240411 | 7/1971 |
| GB | 2108841 | 5/1983 |
| GB | 2159052 | 11/1985 |
| JP | 60005159 | 1/1985 |
| JP | 60005160 | 1/1985 |
| JP | 63005756 | 1/1988 |
| JP | 6354318 | 3/1988 |
| JP | 1-279838 | 11/1989 |
| JP | 2250826 | 10/1990 |
| JP | 3-264522 | 11/1991 |
| JP | 3-264523 | 11/1991 |
| JP | 08325128 A2 | 12/1996 |
| JP | 10-17448 | 1/1998 |
| RU | 2075965 | 9/1994 |
| WO | WO 88/06879 | 9/1988 |
| WO | WO 89/10740 | 11/1989 |
| WO | WO 91/03236 | 3/1991 |
| WO | WO 93/01790 | 2/1993 |
| WO | WO 95/05416 | 2/1995 |
| WO | WO 95/17158 | 6/1995 |
| WO | WO 95/24872 | 9/1995 |
| WO | WO 96/25910 | 8/1996 |
| WO | WO 97/25968 | 7/1997 |
| WO | WO 98//17263 | 4/1998 |
| WO | WO 00/44845 | 8/2000 |
| WO | WO 01/01958 | 1/2001 |
| WO | WO 01/30263 | 5/2001 |

OTHER PUBLICATIONS

3M Dental Products 2000 Product Catalog, 32 pages.
Besner, E., et al., Practical Endodontics, 1994, pp. 7–15, 178–180; Mosby–Year Book, Inc.
S.M. Newman, et al., "Tray–Forming Technique for Dentist–Supervised Home Bleaching", Quintessence International, 1995, pp. 447–453, vol. 26, No. 7.
G. McLaughlin, et al., "Materials" and "Clinical Techniques", Color Atlas of Tooth Whitening, 1991, pp. 35–38 & 45–50, Ishiyaku EuroAmerica, Inc.
R.E. Goldstein, et al., "Chemistry of Bleaching", Complete Dental Bleaching, 1995, pp. 25–32 & 90–97, Quintessence Publshing Co, Inc.
V.B. Haywood, et al., "Nightguard Vital Bleaching", Quintessence International, 1989, vol. 20, No. 3, pp. 173–176, 19$^{th}$ International Meeting on Dental Implants and Transplants, Bologna, Italy.
V.B. Haywood, "History, Safety, and Effectiveness of Current Bleaching Techniques and Applications of the Nightguard Vital Bleaching Technique", Quintessence International, 1992, vol. 23, No. 7, pp. 471–488.
V.B. Haywood, "Nightguard Vital Bleaching", Dentistry Today, 1997, pp. 86–91.
"Tooth Bleaching, Home–Use Products", Clinical Research Associates Newsletter, 1989, vol. 3, Issue 12.
Ralph H. Leonard, Jr. et al, "Risk factors for developing tooth sensitivity and gingival irritation associated with nightguard vital bleaching", Esthetic Dentristy, 1997, vol. 28,No. 8, pp 527–534.

(Continued)

Primary Examiner—Frederick Krass
(74) Attorney, Agent, or Firm—Angela K. Haughey; James C. Vago; Karen F. Clark

(57) ABSTRACT

A tooth whitening product is provided. The tooth whitening product includes a strip of material sized to cover the front surface of one or more teeth and soft tissue adjacent the front surface of the teeth. A thin layer of a tooth whitening composition is disposed on the strip of material. The whitening composition contains a peroxide active with a concentration greater than about 7.5% by weight of the tooth whitening composition, and the tooth whitening composition has a peroxide density less than about 1.3 mg/cm$^2$.

20 Claims, 9 Drawing Sheets

U.S. PATENT DOCUMENTS

| | | |
|---|---|---|
| 3,657,413 A | 4/1972 | Rosenthal et al. |
| 3,688,406 A | 9/1972 | Porter et al. |
| 3,754,332 A | 8/1973 | Warren, Jr. |
| 3,844,286 A | 10/1974 | Cowen |
| 3,902,509 A | 9/1975 | Tundermann et al. |
| 3,955,281 A | 5/1976 | Weitzman |
| 3,972,995 A | 8/1976 | Tsuk et al. |
| 4,138,314 A | 2/1979 | Patil et al. |
| 4,138,814 A | 2/1979 | Weitzman |
| 4,182,222 A | 1/1980 | Stahl |
| 4,211,330 A | 7/1980 | Strock |
| 4,307,075 A | 12/1981 | Martin |
| 4,324,547 A | 4/1982 | Arcan et al. |
| 4,335,731 A | 6/1982 | Bora, Jr. |
| 4,363,843 A | 12/1982 | Crofts |
| 4,376,628 A | 3/1983 | Aardse |
| 4,428,373 A | 1/1984 | Seid et al. |
| 4,431,631 A | 2/1984 | Clipper et al. |
| 4,518,721 A | 5/1985 | Dhabhar et al. |
| 4,522,805 A | 6/1985 | Gordon |
| 4,522,806 A | 6/1985 | Muhlemann et al. |
| 4,528,180 A | 7/1985 | Schaeffer |
| 4,537,778 A | 8/1985 | Clipper et al. |
| 4,544,354 A | 10/1985 | Gores et al. |
| 4,554,154 A | 11/1985 | White |
| 4,557,692 A | 12/1985 | Chorbajian |
| 4,560,351 A | 12/1985 | Osborne |
| 4,568,536 A | 2/1986 | Kronenthal et al. |
| 4,592,487 A | 6/1986 | Simon et al. |
| 4,592,488 A | 6/1986 | Simon et al. |
| 4,661,070 A | 4/1987 | Friedman |
| 4,687,663 A | 8/1987 | Schaeffer |
| 4,696,757 A | 9/1987 | Blank et al. |
| 4,713,243 A | 12/1987 | Schiraldi et al. |
| 4,728,291 A | 3/1988 | Golub |
| 4,741,700 A | 5/1988 | Barabe |
| 4,741,941 A | 5/1988 | Englebert et al. |
| 4,755,385 A | 7/1988 | Etienne et al. |
| 4,755,386 A | 7/1988 | Hsiao et al. |
| 4,765,983 A | 8/1988 | Takayanagi et al. |
| 4,770,634 A | 9/1988 | Pellico |
| 4,786,253 A | 11/1988 | Morais |
| 4,788,052 A | 11/1988 | Ng et al. |
| 4,799,888 A | 1/1989 | Golub |
| 4,812,308 A | 3/1989 | Winston et al. |
| 4,839,156 A | 6/1989 | Ng et al. |
| 4,839,157 A | 6/1989 | Mei-KingNg et al. |
| 4,849,213 A | 7/1989 | Schaeffer |
| RE33,093 E | 10/1989 | Schiraldi et al. |
| 4,895,721 A | 1/1990 | Drucker |
| 4,900,552 A | 2/1990 | Sanvordeker et al. |
| 4,900,554 A | 2/1990 | Yanagibashi et al. |
| 4,902,227 A | 2/1990 | Smith |
| 4,919,615 A | 4/1990 | Croll |
| 4,968,251 A | 11/1990 | Darnell |
| 4,971,782 A | 11/1990 | Rudy et al. |
| 4,972,946 A | 11/1990 | Whittaker |
| 4,980,152 A | 12/1990 | Frazier et al. |
| 4,983,379 A | 1/1991 | Schaeffer |
| 4,983,381 A | 1/1991 | Torres Zaragoza |
| 4,988,500 A | 1/1991 | Hunter et al. |
| 4,990,089 A | 2/1991 | Munro |
| 5,059,417 A | 10/1991 | Williams et al. |
| 5,076,791 A | 12/1991 | Madray, Jr. |
| 5,084,268 A | 1/1992 | Thaler |
| 5,098,303 A | 3/1992 | Fischer |
| 5,122,365 A | 6/1992 | Murayama |
| 5,165,424 A | 11/1992 | Silverman |
| 5,166,233 A | 11/1992 | Kuroya et al. |
| RE34,196 E | 3/1993 | Munro |
| 5,211,559 A | 5/1993 | Hart et al. |
| 5,234,342 A | 8/1993 | Fischer |
| 5,256,402 A | 10/1993 | Prencipe et al. |
| 5,290,566 A | 3/1994 | Schow et al. |
| 5,310,563 A | 5/1994 | Curtis et al. |
| 5,326,685 A | 7/1994 | Gaglio et al. |
| 5,332,576 A | 7/1994 | Mantelle |
| 5,340,314 A | 8/1994 | Tarvis |
| 5,340,581 A | 8/1994 | Tseng et al. |
| 5,356,291 A | 10/1994 | Darnell |
| 5,376,006 A | 12/1994 | Fischer |
| 5,380,198 A | 1/1995 | Suhonen |
| 5,401,495 A | 3/1995 | Murayama |
| 5,409,631 A | 4/1995 | Fischer |
| 5,425,953 A | 6/1995 | Sintov et al. |
| 5,438,076 A | 8/1995 | Friedman et al. |
| 5,472,704 A | 12/1995 | Santus et al. |
| 5,505,933 A | 4/1996 | Norfleet et al. |
| 5,522,726 A | 6/1996 | Hodosh |
| 5,560,379 A | 10/1996 | Pieczenik |
| 5,565,190 A | 10/1996 | Santalucia et al. |
| 5,575,654 A | 11/1996 | Fontenot |
| 5,575,655 A | 11/1996 | Darnell |
| 5,599,553 A | 2/1997 | Chung |
| 5,611,687 A | 3/1997 | Wagner |
| 5,620,322 A | 4/1997 | Lococo |
| 5,626,866 A | 5/1997 | Ebert et al. |
| 5,631,000 A | 5/1997 | Pellico et al. |
| 5,639,445 A | 6/1997 | Curtis et al. |
| 5,662,758 A | 9/1997 | Hamilton et al. |
| 5,678,273 A | 10/1997 | Porcelli |
| 5,700,478 A | 12/1997 | Biegajski et al. |
| 5,707,235 A | 1/1998 | Knutson |
| 5,707,736 A | 1/1998 | Levy et al. |
| 5,713,738 A | 2/1998 | Yarborough |
| 5,723,132 A | 3/1998 | Tseng et al. |
| 5,725,843 A | 3/1998 | Fischer |
| 5,746,598 A | 5/1998 | Fischer |
| 5,759,037 A | 6/1998 | Fischer |
| 5,759,038 A | 6/1998 | Fischer |
| 5,770,105 A | 6/1998 | Fischer |
| 5,770,182 A | 6/1998 | Fischer |
| 5,780,045 A | 7/1998 | McQuinn et al. |
| 5,819,765 A | 10/1998 | Mittiga |
| 5,827,591 A | 10/1998 | Blok et al. |
| 5,846,058 A | 12/1998 | Fischer |
| 5,851,512 A | 12/1998 | Fischer |
| 5,855,870 A | 1/1999 | Fischer |
| 5,858,332 A | 1/1999 | Jensen et al. |
| 5,879,691 A | 3/1999 | Sagel et al. |
| 5,891,453 A | 4/1999 | Sagel et al. |
| 5,894,017 A | 4/1999 | Sagel et al. |
| 5,922,307 A | 7/1999 | Montgomery |
| 5,953,885 A | 9/1999 | Berman et al. |
| 5,968,633 A | 10/1999 | Hamilton et al. |
| 5,980,249 A | 11/1999 | Fontenot |
| 5,985,249 A | 11/1999 | Fischer |
| 5,989,569 A | 11/1999 | Dirksing et al. |
| 6,036,943 A | 3/2000 | Fischer |
| 6,045,811 A | 4/2000 | Dirksing et al. |
| 6,094,889 A | 8/2000 | VanLoon et al. |
| 6,096,328 A | 8/2000 | Sagel et al. |
| 6,136,297 A | 10/2000 | Sagel et al. |
| 6,182,420 B1 | 2/2001 | Berman et al. |
| 6,197,331 B1 | 3/2001 | Lerner et al. |
| 6,277,458 B1 | 8/2001 | Dirksing et al. |
| 6,309,625 B1 | 10/2001 | Jensen et al. |
| 6,322,360 B1 | 11/2001 | Burgio |
| 6,461,158 B1 | 10/2002 | Sagel et al. |
| 6,551,579 B2 | 4/2003 | Sagel et al. |
| 6,582,708 B1 * | 6/2003 | Sagel et al. .......... 424/401 |

OTHER PUBLICATIONS

Van B. Haywood, et al, "Nightguard vital bleaching: how safe is it?", Esthetic Dentistry, 1991, vol. 22, No. 7, pp. 515–523.

Van B. Haywood, "History, safety and effectiveness of current bleaching techniques and applications of the nightguard vital bleaching technique", Esthetic Dentistry, 1992, vol. 23, No. 7, pp. 471–488.

Van B. Haywood, "Bleaching of vital and notvital teeth", Periodontology and Restorative Dentistry, 1992, pp. 142–149.

Van B. Haywood, "Nightquard vital bleaching, a history and products update: Part 1", Esthestic Dentistry Update, 1991, vol. 2, No. 4, pp. 63–66.

Van B. Haywood, "Nightguard vital bleaching, a history and products update: Part 2", Esthestic Dentistry Update, 1991, vol. 2, No. 5, pp. 82–85.

Claudia Paula Drew, "Teeth Bleaching . . . a Vital technique for you to know", Sep./Oct. 1988, pp. 23–25.

Van Benjamin Haywood, "Overview and Status of Mouthguard Bleaching" Journal of Esthetic Dentistry, 1991, vol. 3,No. 5, pp. 157–161.

Van B. Haywood, "Nightguard vital bleaching: current information and research", Esthetic Dentistry Update, 1990, vol. 1, No. 2, pp. 20–25.

Carolyn F. G. Wilson, et al., "Color change following vital bleaching of tetracycline–stained teeth" Pediatric Dentistry, 1985, vol. 7, No. 3, pp. 205–208.

"Tooth Bleaching, Home–Use Products", Clinical Research Associates Newsletter, 1989, pp. 1–4.

Sue Ellen Richardson, "Home bleaching: effectiveness, history, technique, bleaches, cost and safety" The Journal of the Greater Houston Dental Society, 1989, pp. 22–26.

Van B. Haywood, "The food and drug administration and its influence on home bleaching", ADA, 1993, pp. 12–18.

Van B. Haywood, "Efficacy of foam liner in 10% carbamide peroxide bleaching technique", Esthetic Dentistry, 1993, vol. 24, No. 9, pp. 663–666.

Christopher J. Woolverton, "Toxicity of two carbamide peroxide products used in nightguard vital bleaching", American Journal of Dentistry, 1993, vol. 6, No. 6, pp. 310–314.

Van B. Haywood, "Response of normal and tetracycline–stained teeth with pulp–size variation to nightguard vital bleaching", Journal of Esthetic Dentistry, 1994, vol. 6, No. 3, pp. 109–114.

Ralph H. Leonard, et al, "Salivary pH changes during 10% carbamide peroxide bleaching" Dental Research, 1994, vol. 25, No. 8, pp. 547–550.

Ralph H. Leonard, et al, "Change in pH of plaque and 10% carbamide peroxide solution during nightguard vial bleaching treatment" Esthetic Dentistry, 1994, vol. 25, No. 12, pp. 819–823.

Van B. Haywood, "Historical development of whiteners: clinical safety and efficacy", Aesthetics, 1997, pp. 98–104.

Van B. Haywood, "Considerations and variations of dentist–prescribed, home–applied vital tooth–bleaching techniques", Compend Contin Educ Dent, 1994, Suppl.No. 17, pp. s616–s621.

Van B. Haywood, "Effectivness, side effects and long–term status of nightguard vital bleaching", JADA, 1994, vol. 125, pp. 1219–1226.

James W. Curtis, et al, "Assessing the effects of 10 percent carbamide peroxide on oral soft tissues", JADA, 1996, vol. 127, pp. 1218–1223.

Fonda G. Robinson, et al, "Effect of 10 percent carbamide peroxide on color of provisional restoration materials", JADA, 1997, vol. 128, pp. 727–731.

Van B. Haywood, "Commonly asked questions about nightguard vital bleaching", IDA Journal, 1993, pp. 28–33.

Van B. Haywood, "Nightguard vital bleaching: current concepts and research", JADA, 1997, vol. 128, pp. 19s–25s.

Van B. Haywood, "Commonly asked questions about nightguard vital bleaching", The Dental Assistant, Mar./Apr. 1996, pp. 6–12.

M.S. McCracken, "Demineralization effects of 10 percent carbamide peroxide", Journal of Dentistry, 1996, vol. 24, No. 6, pp. 395–398.

Messing, J.J., et al., Color Atlas of Endodontics, 1988, pp. 106–107, 135–140, 173–175, 257–259; The C.V. Mosby Company, Ltd.

Van B. Haywood, "Efficacy of six months of nightguard vital bleaching of tetracycline–stained teeth", Journal of Esthetic Dentistry, 1997, vol. 9 , No. 1, pp. 13–19.

Van B. Haywood, "Achieving, maintaining and recovering successful tooth bleaching", Journal of Esthetic Dentistry, 1996, vol. 8, No. 1, pp. 31–38.

Carl M. Russell, et al, "Dentist–supervised home bleaching with ten percent carbamide peroxide gel: a six month study", Journal of Esthetic Dentistry, 1996, vol. 8, No. 4, pp. 177–182.

Van B. Haywood, "Historical development of whiteners: clinical safety and efficacy", Aesthetics, 1997 April update, pp. 98–104.

Office Action from the United States Patent & Trademark Office, dated Sep. 5, 2002, issued on U.S. Appl. No. 09/864,686, filed May 24, 2001, assignee—The Procter & Gamble Company, now abandoned.

Office Action from the United States Patent & Trademark Office, dated May 28, 2003, issued on U.S. Appl. No. 09/864,686, filed May 24, 2001, assignee—The Procter & Gamble Company, now abandoned.

Declaration under 37 CFR § 1.131—Paul Albert Sagel (2005).

* cited by examiner

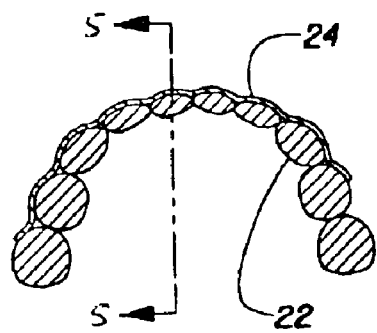
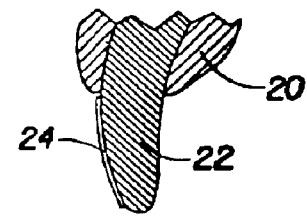
Fig. 4  Fig. 5
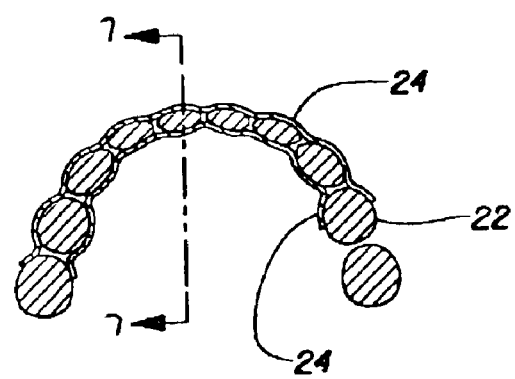
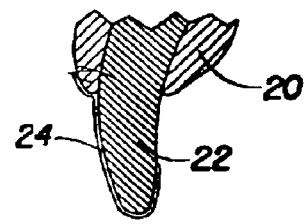
Fig. 6  Fig. 7

TOOTH WHITENING PRODUCTS

TECHNICAL FIELD OF THE INVENTION

The present invention relates to products for whitening teeth, and, more particularly, to tooth whitening products having improved whitening efficacy.

BACKGROUND OF THE INVENTION

Many approaches are used to whiten teeth. Two of the most common approaches use abrasives or chemical whiteners, such as peroxides. Abrasives in combination with a polishing action are used to polish discolorations and stains off of the surface of the teeth. Thus, light reflected from the teeth represents the true intrinsic color of the teeth. Abrasives are a major element of most consumer toothpastes and prophyaxis pastes used by dentists. Because abrasives only work on the surface of the teeth, the intrinsic color of the tooth is largely unchanged. As such, abrasives only offer limited effectiveness in whitening of the teeth.

The second approach is the use of chemical whitening actives in a composition to intrinsically and extrinsically whiten teeth. Chemical whitening actives are applied to the teeth for period of time to allow the active to act upon the tooth and provide an improvement in the whiteness of the teeth. Whiteners are commonly applied to the teeth using toothpastes, rinses, gums, floss, tablets, strips and trays. A common chemical whitening active is peroxide. Often, strips and trays are used to apply peroxide for contact times beyond that achievable with typical toothbrushing. Concentration of the whitening active, contact time and number of applications are some of the primary parameters which dictate the rate and amount of whitening achieved with peroxide based tooth whitening compositions. Whitening products using a strip of material in combination with a chemical whitening active are known in the art. For example, U.S. Pat. Nos. 5,891,453 and 5,879,691, the substances of which are incorporated herein by reference, describe a whitening product comprising a flexible strip of material and a whitening composition. The whitening composition can include a peroxide active.

It is commercially desirable to increase the whitening efficacy of products in order to deliver a more satisfying product experience. Increasing the concentration of peroxide, holding all other parameters essentially constant, generally results in faster whitening per time of use. Similarly, longer contact times produce more whitening provided the peroxide is maintained on the tooth surface. Thus, increasing concentration, increasing wear time and increasing number of applications can be effective methods of achieving higher degrees of tooth whitening from a tooth whitening product. Each of these parameters also may have a negative impact on the consumer's experience. Increasing the concentration of the peroxide in the whitening composition, holding all other parameters essentially constant, can produce more tooth sensitivity and cause more soft tissue irritation. Sufficiently high concentrations of peroxide may require a physical barrier, such as a rubber dam, to prevent the peroxide from contacting and burning the soft tissue thereby making the use of the high peroxide concentrations inconvenient and impractical for unsupervised at home and repeated use. In fact, even conventional chairside tooth whitening compositions having a peroxide concentration equivalent to 13% hydrogen peroxide often utilize a rubber dam to protect the soft tissue during the bleaching process. Increasing the use time will increase the amount of tooth sensitivity and gingival irritation as well as make the product more inconvenient to use. Similarly, increasing the number of uses also makes the product less convenient to use.

Thus, there is a desire to provide whitening products that achieve the increased whitening efficacy associated with increased peroxide concentrations while avoiding attendant soft tissue irritation so often associated with these higher peroxide levels. Still further, there is a desire to provide convenient tooth whitening products that utilize higher peroxide concentrations without the need for artificial barriers, such as rubber dams or other ginigival protectants.

SUMMARY OF THE INVENTION

A tooth whitening product is provided. The tooth whitening product includes a strip of material sized to cover the front surface of one or more teeth and soft tissue adjacent the front surface of the teeth. A thin layer of a tooth whitening composition is disposed on the strip of material. The tooth whitening composition contains a peroxide active with a concentration greater than about 7.5% by weight of the whitening composition, and the tooth whitening composition has a peroxide density less than about 1.3 mg/cm$^2$.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

FIG. 4 is a cross-sectional plan view of human dentition, illustrating application of a tooth whitening product of the present invention to the front surface of a plurality of teeth;

FIG. 5 is a cross-sectional side elevation view of a tooth of FIG. 4 taken along line 5—5 thereof;

FIG. 6 is a cross-sectional plan view, similar to FIG. 4, showing a tooth whitening product of the present invention applied to front and back surfaces of a plurality of teeth;

FIG. 7 is a-cross-sectional side elevation view of FIG. 6 taken along line 7—7 thereof, showing a tooth whitening product of the present invention conforming to front and back tooth surfaces of a plurality of teeth and adjoining soft tissue;

DETAILED DESCRIPTION OF THE PREFERRED EMBODIMENTS

Figure 8:
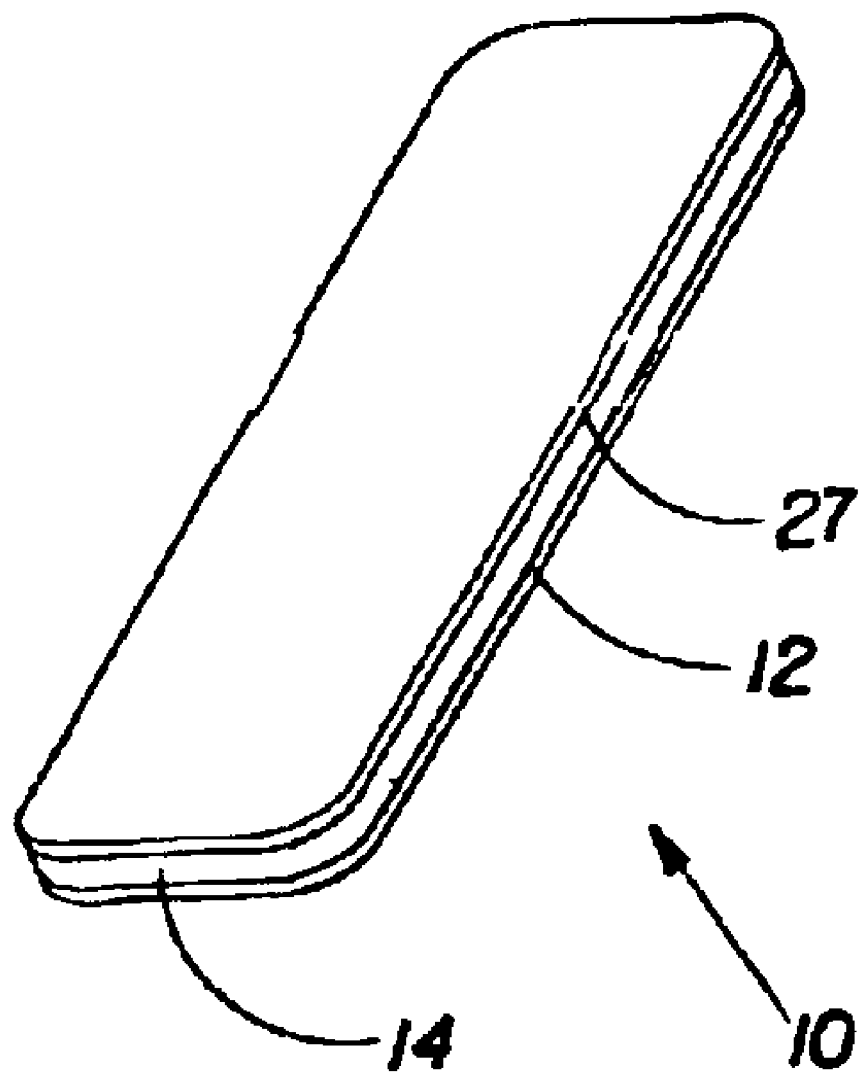
FIG. 8 is a perspective view of an alternative embodiment of the tooth whitening product of the present invention, wherein the tooth whitening product includes a release liner.

Reference will now be made in detail to the present preferred embodiments of the invention, examples of which are illustrated in the accompanying drawings wherein like numerals indicate the same elements throughout the views and wherein elements having the same two last digits (e.g., 20 and 120) connote similar elements. All percentages herein are expressed as percent weight of the tooth whitening composition unless stated otherwise. Referring to FIGS. 1 to 8, several exemplary embodiments of the present invention will now be described. The tooth whitening product 10 comprises a strip of flexible material 12, a thin layer 14 of a tooth whitening composition having a peroxide active, and optionally a release liner 27 (FIG. 8). The strip of material 12 is used to apply the tooth whitening composition to the teeth and serves as a protective barrier to substantially prevent saliva from contacting the tooth whitening composition as well as preventing erosion of the tooth whitening composition from the surface of the teeth by the wearer's lips, tongue, and other soft tissue. The release liner 27 also serves as a protective barrier, but the strip of material 12 and the thin layer 14 are separated from the release liner 27 prior to application of the tooth whitening composition to the teeth, thereby exposing the thin layer 14 for use.

The strip of material 12 is sized to cover the front or labial/buccal surface of one or more teeth, as best seen in FIGS. 4 and 6. In another embodiment, the strip of material is sized to cover the front surface of a plurality of teeth as well as at least some of the soft tissue adjacent those teeth. As used herein, the phrase "soft tissue" is intended to refer to one of the gingival margins. In another embodiment, the strip of material is sized to cover the front surface of a plurality of teeth, at least some soft tissue adjacent the plurality of teeth, and at least some of the back or lingual surface of the plurality to teeth, as best seen in FIG. 7. Generally, the strip of material is sized to cover the front, six to eight teeth of the upper or lower rows of teeth that are visible when the wearer is smiling or either the maxillary dentition or the mandibular dentition. Optionally, the strip of material 12 may fit the entire upper or lower rows of teeth when positioned against the teeth. Most preferably, the strip of material 12 is sized to overlap with and is further sized to cover at least the central six anterior teeth (cuspid to cuspid). The strip of material 12 can be a maxillary strip which is rectangular with rounded corners and measures approximately 6.5 cm long × 1.5 cm wide and/or the strip of material 12 can be a mandibular strip which is trapezoidal with rounded corners and measures 5 cm long × 2 cm wide. Further description of the size and shape of the strip of material 12 in a tooth whitening application is disclosed in U.S. patent application Ser. No. 09/268,185 filed Mar. 15, 1999, now abandoned the substance of which is fully incorporated herein by reference. Other shapes and sizes for the strip of material would also be suitable. Further, it is contemplated that the present invention could be applied to other tooth whitening applicators such as bleaching trays (e.g., such as described in U.S. Pat. Nos. 5,846,058; 5,816, 802; and 5,895,218), permanently deformable strips (e.g., such as that described in U.S. Pat. No. 6,045,811), and other pre-loaded devices (e.g., such as that described in U.S. Pat. No. 5,310,563), the substances of which are incorporated herein by reference. The strip of material can include a plurality of pockets 18 (FIG. 3) which are filled with the tooth whitening composition.

Figure 9:
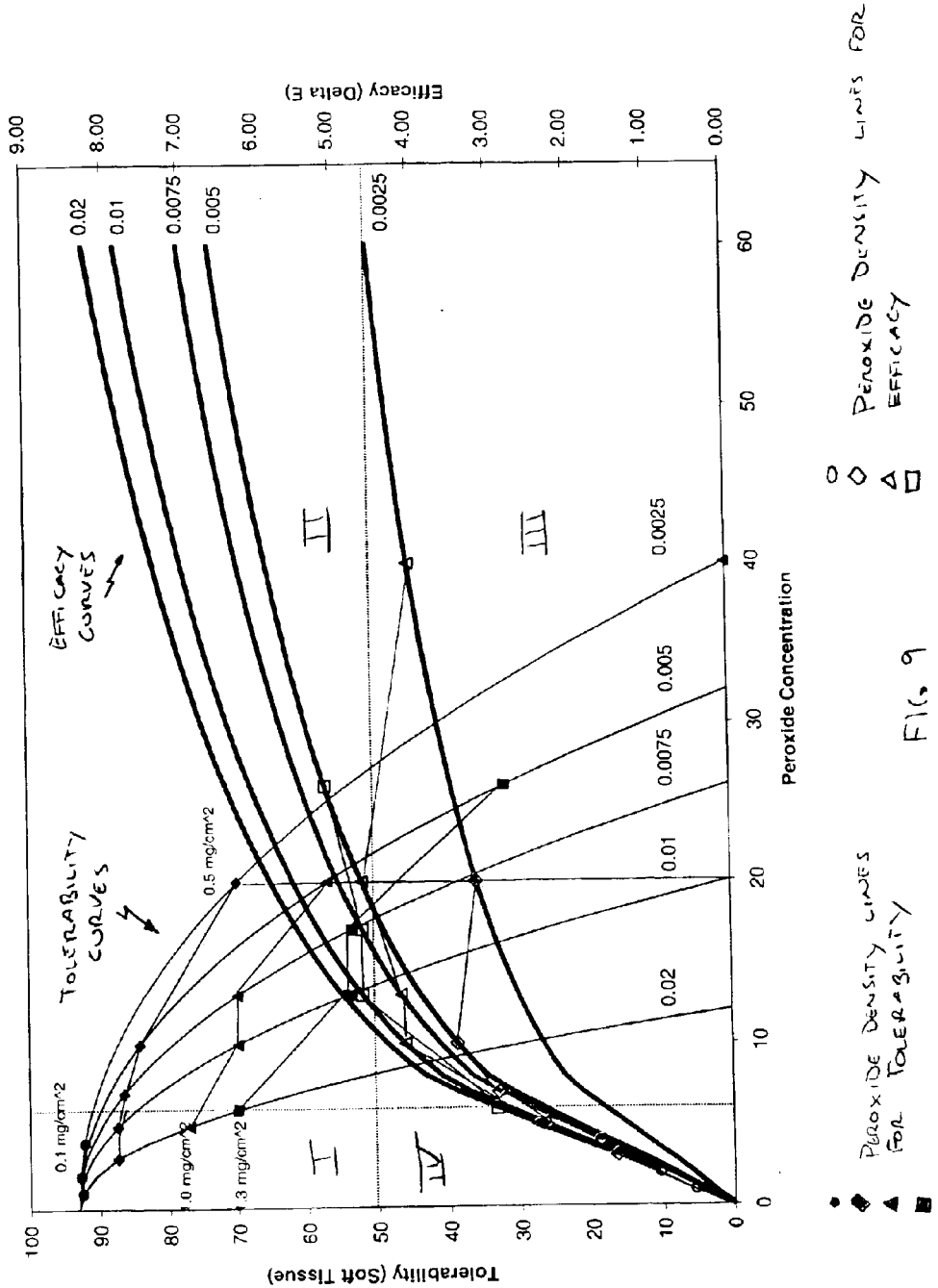
FIG. 9 is a graph illustrating the interplay between whitening efficacy, soft tissue tolerability, peroxide concentration, composition loading and peroxide dosing.

Referring to FIG. 9 and in accordance with one aspect of the present invention, it is has been found that relatively high peroxide concentrations can be used to provide improved whitening efficacy over current flexible, strip-based whitening products, such as Crest Whitestrips® manufactured by the Procter & Gamble Company, Cincinnati, Ohio, while still maintaining acceptable soft tissue tolerability without the need for cumbersome rubber dams or other artificial soft tissue barriers. As used herein, the phrase "artificial barrier" is intended to refer to any physical means that prevents or is intended to prevent a whitening composition from migrating onto the soft tissue adjacent the teeth during a bleaching operation. Other artificial barriers can include light cured resins.

As used herein, the phrase "soft tissue tolerability" is intended to refer to the degree to which a product user experiences a sensation often described as burning or stinging or experiences irritation of the gingival tissues. This sensation can range from minor to severe. While a minor sensation is noticeable, a user is able to complete a consecutive two week, twice a day for thirty minutes, regimen using the subject whitening product without difficulty. A severe sensation often causes a user to discontinue the regimen prior to its completion due to the discomfort. Soft tissue tolerability for a whitening product can be determined by surveying a representative sample of users, such as one hundred individuals, for such sensations following completion or attempted completion of the specified regimen. Alternatively, direct observation of the soft tissue can be performed to detect any instances of soft tissue irritation. While it is desirable to minimize the number of individuals which experience any of the above-described sensations, their complete elimination can be difficult to achieve due to the subjectivity involved in their assessment and the susceptibility of some individuals to these sensations even with nominal peroxide active concentrations.

Figure 10:
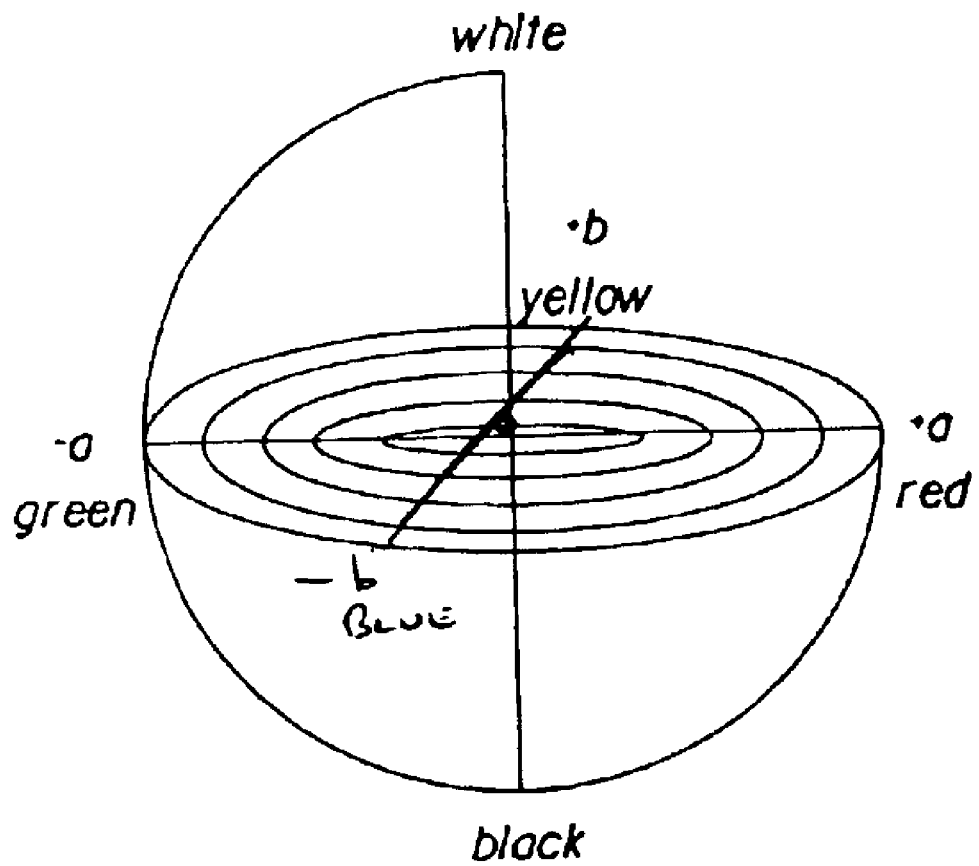
FIG. 10 is a schematic illustration of the 1976 CIE LAB color space.

As used herein the phrase "whitening efficacy" is intended to refer to the amount of change in tooth color. The color change can be measured according to the LAB color scale. FIG. 10 illustrates a model of the 1976 CIE LAB color space. The L* value measures brightness and varies from a value of one hundred for perfect white to zero for black assuming a* and b* are zero. The a* value is a measure redness when positive, gray when zero and greenness when negative. The b* value is a measure of yellowness when positive, gray when zero and blueness when negative. Generally, teeth appear whiter as: the L value increases meaning they become brighter, the a* value increases or decreases depending upon whether the stained teeth have a green or red tint prior to whitening, and the b* value decreases meaning they become less yellow. While this is the general relationship for perceived whitening, the b* value might also slightly increase if the magnitude of the increase of the L* value is large enough. Similarly, the L value might also decrease if the magnitude of the decrease of the b* value is large enough to overshadow the less significant change in L*. Because the color of actual stained teeth varies by different geographies, whether the a* value increases or decreases for whitening can be geography dependent. For instance, stained teeth have a brown or red tint in the United States while stained teeth have a green tint in China.

The overall color change can be determined by the following equation for delta E (ΔE):

$$\Delta E = (\Delta L^{*2} + \Delta a^{*2} + \Delta b^{*2})^{1/2}$$

When ΔL is positive, Δb* is negative and a* is moving towards zero, ΔE represents an improvement in tooth whiteness. ΔE is a scalar value, and therefore it represents the magnitude of the color change, but not the direction. For that reason, the direction of the changes in the individual color components L*, a* and b* must be evaluated to determine whether the ΔE value represents an improvement in tooth whiteness. A method for measuring whitening efficacy, as expressed by ΔE, is discussed more fully hereafter.

Referring again to FIG. 9 and while not intending to be bound by any theory, there is illustrated a relationship between whitening efficacy, soft tissue tolerability, peroxide concentration, and whitening composition loading. Generally, as peroxide concentration increases, whitening efficacy increases as shown by the upward slope of the efficacy lines of the graph of FIG. 9. Each efficacy line represents a line of iso-composition loading (i.e., a line of constant composition loading). Efficacy lines are shown for composition loadings of 0.0025 gm/cm², 0.005 gm/cm², 0.0075 gm/cm², 0.01 gm/cm², and 0.02 gm/cm². The phrase "composition loading" is intended to refer to the ratio of the amount of tooth whitening composition (gm) to the surface area (cm²) of the thin layer 14 that is applied to the tooth surfaces and adjacent soft tissue of the oral cavity. This surface area may be different than the "exposed surface area" and/or "unexposed surface area" which are discussed hereafter. Generally, soft tissue tolerability decreases as peroxide concentration increases, as shown by the downward slope of the tolerability lines of the graph of FIG. 9. Each tolerability line also represents a line of iso-composition loading (i.e., a line of constant composition loading). Tolerability lines are shown for composition loadings of 0.0025 gm/cm², 0.005 gm/cm², 0.0075 gm/cm², 0.01 gm/cm², and 0.02 gm/cm². From this family of curves, it will be appreciated that it is possible to maintain acceptable soft tissue tolerability while increasing whitening efficacy by increasing the peroxide concentration to relatively high levels if there is an appropriate decrease in composition loading. Stated another way, it is possible to increase the concentration of the peroxide active to achieve improved whitening efficiency while maintaining acceptable soft tissue tolerability, without the use of artificial barriers, by properly selecting the composition loading.

This relationship can also be characterized by a parameter, peroxide density, which is the ratio of the amount of peroxide active (mg) or peroxide dose to the surface area (cm²) of the thin layer that is applied to the tooth surfaces and adjacent soft tissue of the oral cavity. This surface area may be different than the "exposed surface area" and/or "unexposed surface area" which are discussed hereafter. Several lines of constant peroxide density are shown in FIG. 9, including 0.5 mg/cm², 0.1 mg/cm², 1 mg/cm², and 1.3 mg/cm². There is one family of peroxide density lines plotted with respect to the tolerability lines and there is one family of peroxide density lines plotted with respect to the efficacy lines. In most instances, the surface area of the thin layer can be approximated by the surface of the strip of material if the entire strip of material is applied to the oral cavity and if the entire strip of material is coated with the thin layer of the tooth whitening composition. For example, if the strip of material is rectangular and has a length of 6.5 cm and width of 1.54 cm and the thin layer of tooth whitening composition is coated over an entire side of the strip of material, the total surface area is 10 cm². If the tooth whitening composition contains 6.5% hydrogen peroxide and the strip of material contains 0.2 gm of the tooth whitening composition, then the hydrogen peroxide dose is 13 mg. The corresponding peroxide density is 1.3 mg/cm².

Thus, for a given peroxide concentration and whitening composition loading, there is a given efficacy and tolerability shown in FIG. 9. For example, at a peroxide concentration of 20% and a whitening composition loading of 0.0025 gm/cm², the peroxide density is 0.5 mg/cm², the tolerability is about 70% (meaning that, on average, 70% of individuals may report no burning or stinging sensations), and the efficacy is about 3 units (delta E). Both peroxide density points (i.e., on both the efficacy and tolerability curves) are shown in FIG. 9.

In one embodiment, so long as the peroxide density is less than about 1.3 mg peroxide/cm², there can be an acceptable tradeoff between soft tissue tolerability and whitening efficacy for peroxide concentrations greater than at least about 7.5%. While extremely high peroxide concentrations can be surprisingly utilized with the present invention, generally it is desirable to utilize peroxide concentrations less than 60% and, even more desirable to have a peroxide density (with respect to the tolerability lines) in the upper two quadrants I and II of FIG. 9 for tooth whitening applications, because the soft tissue tolerability is acceptable to very good. For peroxide densities in quadrant I (as plotted on the tolerability curves), generally the whitening efficacy will be less than peroxide densities in quadrant II, because, while the composition loading is low enough in quadrant I that soft tissue tolerability is acceptable, the composition loading is so low that whitening efficacy may drop off substantially, as shown by the corresponding peroxide density points plotted on the efficacy curves. The peroxide density line of 1.3 mg/cm² represents one boundary where meaningful to very good whitening efficacy occurs with acceptable to very good soft tissue tolerability.

In other embodiments, the peroxide density is less than about 1.2 mg/cm², or less than about 1.1 mg/cm², or less than about 1 mg/cm², or less than about 0.75 mg/cm², or less than about 0.5 mg/cm², and/or greater than about 0.01 mg/cm² or greater than about 0.1 mg/cm², or greater than about 0.25 mg/cm², or greater than about 0.5 mg/cm² in combination with a peroxide concentration greater than about 7.5%, or greater than about 8%, or greater than about 10%, or greater than about 12%, or greater than about 16%, or greater than about 20%, and/or less than about 40%, or less than about 35%, or less than about 30%, or less than about 20%. The peroxide active can be any form that liberates peroxide either by soluabilization or hydration. All peroxide active concentrations expressed herein are for hydrogen peroxide and appropriate conversions must be made for other peroxide liberating molecules such as carbamide peroxide, calcium peroxide and sodium percarbonate, etc. Some other peroxide actives suitable for use with the present invention include calcium peroxide, carbamide peroxide, sodium percarbonate, benzoyl peroxide and mixtures thereof. A method for determining the concentration of the peroxide active is set forth hereafter. The above-described peroxide concentrations and peroxide densities are the concentrations and densities at the time of application of the tooth whitening product to the oral cavity.

In another embodiment, characterized by a portion of quadrant III of FIG. 9, the peroxide density is between about 1.3 mg/cm$^2$ and about 2.4 mg/cm$^2$ in combination with a peroxide concentration greater than about 7.5%, or greater than about 8%, and less than about 16% or less than about 12%. In this embodiment, there can be an acceptable, albeit not as preferred, balance of whitening efficacy and soft tissue tolerability.

The total amount of the tooth whitening composition that is delivered to the oral cavity will vary depending upon the size of the strip of material 12 and the concentration of the peroxide active. Generally, greater than about 0.0002 gram of tooth whitening composition is provided with the present invention, or greater than about 0.005 gm, or greater than about 0.01 gm, or greater than about 0.015 gm, or greater than about 0.02 gm, or greater than about 0.025 gm, or greater than about 0.05 gm, or greater than about 0.075 gm, or greater than about 0.1 gm, or greater than about 0.15 gm, or greater than about 0.2 gm and/or less than about 0.3 gm, or less than about 0.2 gm, or less than about 0.15 gm, or less than about 0.1 gm, or less than about 0.05 gm, or less than about 0.025 gm, or less than about 0.001 gm.

The tooth whitening composition loading is greater than about 0.0005 gm/cm$^2$, or greater than about 0.001 gm/cm$^2$, or greater than about 0.002 gm/cm$^2$, or greater than about 0.0025 gm/cm$^2$, or greater than about 0.005 gm/cm$^2$, or greater than about 0.0075 gm/cm$^2$, or greater than about 0.01 gm/cm$^2$, or greater than about 0.015 gm/cm$^2$, and/or less than about 0.03 gm/cm$^2$, or less than about 0.02 gm/cm$^2$, or less than about 0.015 gm/cm$^2$, or less than about 0.01 gm/cm$^2$, or less than about 0.005 gm/cm$^2$, or less than about 0.001 gm/cm$^2$.

As previously discussed, the tooth whitening composition contains a peroxide active and is provided in the thin layer 14 between the release liner 27 and the strip of material 12. The thin layer 14 of tooth whitening composition is generally on or in contact with the strip of material 12 and release liner 27. In order to achieve the previously described composition loadings at the higher peroxide concentrations, the thin layer 14 of tooth whitening composition that is applied to the oral cavity may have a thickness less than about 0.3 mm, or less than about 0.2 mm, or less than about 0.15 mm, or less than about 0.1 mm, or less than about 0.06 mm, or less than about 0.03 mm, or less than about 0.001 mm and/or greater than about 0.0002 mm, or greater than about 0.004 mm, or greater than about 0.008mm, or greater than about 0.016 mm, or greater than about 0.018 mm, or greater than about 0.02 mm, or greater than about 0.1 mm, or greater than about 0.15 mm. These measurements are taken by measuring from the surface 28 (FIG. 2) of the strip of material 12 and up through the thin layer 14 of tooth whitening composition.

The peroxide dose, which is the total amount of the peroxide active within the thin layer of the tooth whitening composition that is applied to the oral cavity, is less than about 100 mg, or less than about 95 mg, or less than about 85 mg, or less than about 80 mg, or less than about 40 mg, or less than about 20 mg, or less than about 15 mg, or less than about 12 mg, or less than about 10 mg, or less than about 5 mg, or less than about 1 mg, and/or greater than about 0.1 mg, or greater than about 0.3 mg, or greater than about 0.6 mg, or greater than about 1 mg, or greater than about 1.5 mg, or greater than about 2 mg, or greater than about 10 mg.

While it is desirable for the thin layer of the tooth whitening composition to be a homogeneous, uniform and continuous layer, the thin layer 14 may also be non-uniform, non-continuous, and/or heterogeneous. For example, the thin layer 14 can be a laminate or separated layers of components, an amorphous mixture of components, separate stripes or spots or other patterns of different components, or a combination of these structures.

The tooth whitening composition of the present invention can be provided in the form of a viscous liquid, paste, gel, solution, or any other state or phase that can form a thin layer. The tooth whitening composition can be provided in the form of a gel with a viscosity between about 200 and about 1,000,000 cps at low shear rates (approximately one seconds$^{-1}$). In another embodiment, the viscosity is between about 100,000 and about 800,000 cps or between about 150,000 and about 700,000 cps. In yet another embodiment, the viscosity is between about 300,000 and about 700,000 cps.

As known in the art, the tooth whitening composition also has a yield stress. Yield stress is the amount of force on a material before the material begins to move. The yield stress must be high enough so that the tooth whitening composition is able to form a thin layer and also to handle the disturbances caused by manufacturing, handling, and storage. The yield stress of the tooth whitening composition is between about 2 Pascals and about 3000 Pascals, preferably between about 20 Pascals and about 2000 Pascals, more preferably between about 200 Pascals and about 1500 Pascals, and most preferably between about 400 Pascals and about 200 Pascals.

Additional constituents of the tooth whitening composition can include, but are not limited to, water, gelling agents, humectants, pH adjusting agents, stabilizing agents, desensitizing agents, and accelerating agents or bleach activators. In addition to the above materials, a number of other materials can also be added to the substance. Additional materials include, but are not limited to, flavoring agents, sweetening agents such as saccharin, xylitol, opacifiers, coloring agents, and chelants such as ethylenediaminetetraacetic acid. These additional ingredients can also be used in place of the compounds disclosed above.

Gelling agents suitable for use do not react with or inactivate the constituents of the oral care composition. A common gelling agent is a swellable polymer. An effective concentration of a gelling agent to enable the tooth whitening composition to form a thin layer will vary with each type of gelling agent. The thin layer will have a viscosity and yield stress enabling the tooth whitening composition to form the thin layer on a release liner. The tooth whitening composition formed with these agents may also provide sufficient adhesive attachment of the film material to the targeted area of the mouth. For example, the level of gelling agent to form the tooth whitening composition composition with a carboxypolymethylene is between about 0.1% and about 15%, preferably between about 1% and about 10%, more preferably between about 2% and about 8%, and most preferably between about 3% and about 6%, by weight of the tooth whitening composition. An effective concentration of a poloxamer gelling agent is between about 10% and about 40%, preferably between about 20% and about 35%, and more preferably between about 25% and about 30%, by weight of the tooth whitening composition.

Suitable gelling agents useful in the present invention include "Pemulen" made by B. F. Goodrich Company, carboxypolymethylene, carboxymethyl cellulose, carboxypropyl cellulose, hydroxyethyl cellulose, poloxamer, Laponite, carrageenan, Veegum, carboxyvinyl polymers, and natural gums such as gum karaya, xanthan gum, Guar gum, gum arabic, gum tragacanth, and mixtures thereof. The preferable gelling agent for use in the present invention is carboxypolymethylene, obtained from B. F. Goodrich Company under the tradename "Carbopol". Particularly preferable Carbopols include Carbopol 934, 940, 941, 956, 971, 974, 980, and mixtures thereof. Particularly preferred is Carbopol 956. Carboxypolymethylene is a slightly acidic vinyl polymer with active carboxyl groups.

Other suitable gelling agents include both polymers with limited water solubility as well as polymers lacking water solubility. Suitable limited water solubility adhesives include: hydroxy ethyl or propyl cellulose. Adhesives lacking water solubility include: ethyl cellulose and polyox resins. Another possible adhesive suitable for use in the instant composition is polyvinylpyrrolidone with a molecular weight of about 50,000 to about 300,000. Still another possible adhesive suitable for use in the instant composition is a combination of Gantrez and the semisynthetic, water-soluble polymer carboxymethyl cellulose.

A pH adjusting agent may also be added to make the composition safe for oral tissues. These pH adjusting agents, or buffers, can be any material that is suitable to adjust the pH of the composition. Suitable materials include sodium bicarbonate, sodium phosphate, sodium hydroxide, ammonium hydroxide, potassium hydroxide, sodium stannate, triethanolamine, citric acid, hydrochloric acid, sodium citrate, and combinations thereof. The pH adjusting agents are added in sufficient concentrations so as to adjust the pH of the composition to between about 3 and about 10, preferably between about 4 and about 8.5, and more preferably between about 4.5 and about 8. The pH adjusting agents are generally present in an concentration between about 0.01% and about 15% and preferably between about 0.05% and about 5%, by weight of the composition.

Suitable stabilizing agents include benzoic acid, salicylic acid, butylated hydroxytoluene, tin salts, phosphates, and others. Suitable bleach activators include trichloroisocyanuric acid and the phosphates, such as tetrasodium pyrophosphate.

Desensitizing agents may also be used in the tooth whitening composition. These agents may be preferred for consumers who have sensitive teeth. Desensitizing agents include potassium nitrate, citric acid, citric acid salts, strontium chloride, and combinations thereof. Potassium nitrate is a preferred desensitizing agent. Other agents which provide the benefit of reduced tooth sensitivity are also included in the present invention. Typically, the concentration of a desensitizing agent is between about 0.01% and about 10%, preferably between about 0.1% and about 8%, and more preferably between about 1% and about 7% by weight of the tooth whitening composition.

The strip of material 12 may be formed from materials such as polymers, natural and synthetic wovens, non-wovens, foil, paper, rubber, and combinations thereof. The strip of material 12 (as well as the release liner 27) may be a single layer of material or a laminate of more than one layer. Suitable polymers include, but are not limited to, ethylvinylacetate, ethylvinyl alcohol, polyesters such as MYLAR® manufactured by DuPont, and combinations thereof.

Figure 1:
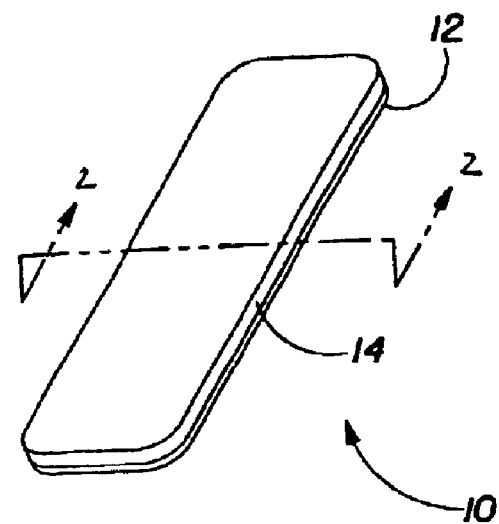
FIG. 1 is a perspective view of one embodiment of a tooth whitening product of the present invention comprising a substantially flat strip of material having a tooth whitening composition coated thereon.
Figure 2:
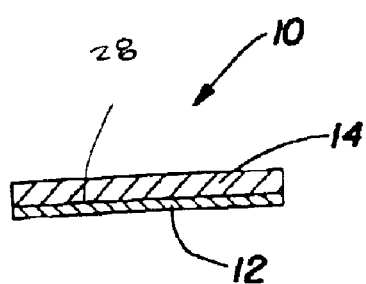
FIG. 2 is cross-sectional side elevation view of the tooth whitening product of FIG. 1 taken along line 2—2 thereof.
Figure 3:
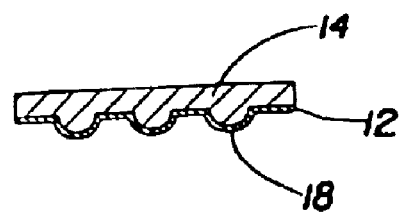
FIG. 3 is a cross-sectional side elevation view showing an alternative embodiment of the present invention, wherein the strip of material has a plurality of shallow pockets.

The release liner can be formed from any material that exhibits less affinity for the tooth whitening composition than the tooth whitening composition exhibits for itself and for the strip of material 12. For example, the release liner 27 can be formed from paper or a polyester, such as SCOTCHPAK® which is manufactured by the 3M Corp. of Minneapolis, Minn., which are coated with a non-stick material in order to aid release of the tooth whitening composition from the release liner 27 when the strip of material 12 is pulled away from the release liner 27. Exemplary coatings can include wax, silicone, fluoropolymers such as Teflon®, fluorosilicones, or other non-stick type materials. Also, suitable coatings might include one of the coatings described in U.S. Pat. Nos. 3,810,874; 4,472,480; 4,567,073; 4,614,667; 4,830,910; and 5,306,758, the substances of which are incorporated herein by reference. A further description of materials suitable which might be suitable as release agents is found in Kirk-Othmer Encyclopedia of Chemical Technology, Fourth Edition, Volume 21, pp. 207–218, incorporated herein by reference. The release liner 27 should be at least the same size and shape as the strip of material 12 as shown in FIG. 1. However, the release liner 27 can extend beyond the strip of material so that it is easier to the release liner 27 and remove the strip of material 12 and the thin layer 14 from the release liner 27.

While the tooth whitening product 10 is described herein as comprising both the strip of material 12 and the release liner 27, it is contemplated that the tooth whitening product 10 may comprise only the strip of material 12 and the thin layer 14. For example, the interior of a package storing the strip of material 12 and the thin layer 14 might be coated in a manner similar to that described above with respect to the release liner 27 to facilitate removal of the strip of material 12 and the thin layer from the package during use. Further, it is contemplated that the tooth whitening product 10 could be provided in the form of a roll rather than planar as shown herein and could comprise a plurality of strip of materials and/or release liners. Alternatively, it is contemplated that the strip of material 12 and/or release liner 27 might include other non-planar shapes such as preformed dental trays or flexible dental trays. The strip of material and/or release liner can also be formed from permanently deformable strips of material, wax, or any other material suitable for use as a barrier for the tooth whitening composition and for applying the tooth whitening composition to the teeth.

While the above-described materials for the strip of material 12 and release liner 27 are suitable for use with the present invention, the stability of the peroxide active of the thin layer 14 of the tooth whitening composition can be improved when the release liner 27 and/or the strip of material 12 (or at least the surfaces in contact with the peroxide active) are formed from a polyolefin and, preferably, from polyethylene or polypropylene. Even small to moderate increases in the stability of a peroxide active can have a significant impact on the shelf life of a tooth whitening product. As used herein, the term "stability" is intended to refer to the propensity of a peroxide active to maintain its original concentration over a specified period of time (e.g., 3 months, 6 months, 12 months), wherein the specified period of time is measured beginning from the point at which the tooth whitening composition is manufactured and formed as a thin layer. Other polyolefin blends, polyethylene blends, polypropylene blends, and combinations thereof would also be suitable for use as the strip of material 12 and/or the release liner 27 in the present invention. As discussed above, the release liner 27 can also be coated to aid release of the tooth whitening composition from the release liner 27 during manufacture and/or use. However, these coatings generally do not act as barriers between the peroxide active and underlying material such that proper selection of the underlying material is still desirable. Any coating should be inert, however, relative to the peroxide active.

The strip of material 12 and/or release liner 27 are generally less than about 1 mm thick, preferably less than about 0.05 mm thick, and more preferably from about 0.001 to about 0.03 mm thick. Still more preferably, the strip of material 12 and/or release liner 27 are less than about 0.1 mm thick and yet more preferably from about 0.005 to about 0.02 mm thick. The thickness and the permeability of the strip of material 12 and/or release liner 27 may have an effect on the stability of the tooth whitening composition. In general, a thicker strip may provide more stability for the tooth whitening composition. However, the thickness of the strip of material must be balanced with the consumer acceptance of comfort of wearing the strip.

The strip of material 12 should have a relatively low flexural stiffness so as to enable it to drape over the contoured surfaces of the teeth with very little force being exerted; that is, conformity to the curvature of the wearer's mouth, teeth, and gaps between teeth is maintained because there is little residual force within the strip of material to cause it to return to its substantially flat shape. The flexibility of the strip of material enables it to contact adjoining soft tissue over an extended period of time without physical irritation. The strip of material does not require pressure to form it against the teeth and it is readily conformable to the tooth surfaces and the interstitial tooth spaces without permanent deformation when it is applied.

Flexural stiffness is a material property that is a function of a combination of strip thickness, width, and material modulus of elasticity. This test is a method for measuring the rigidity of polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter, wired to the strain gauge is calibrated in grams of deflection force. The rigidity of the sample is read directly from the microammeter and expressed as grams per centimeter of sample strip width. In a preferred embodiment but not required for the present invention, the flexible strip of material has a flexural stiffness of less than about 5 grams/cm as measured on a Handle-O-Meter, model #211-300, available from Thwing-Albert Instrument Co. of Philadelphia, Pa., as per test method ASTM D2923-95. Preferably, the strip of material 12 has a flexural stiffness less than about 4 grams/cm, more preferably less than about 3 grams/cm, and most preferably from about 0.1 grams/cm to about 1 grams/cm.

For a tooth whitening composition, it is often desirable to include a humectant as a constituent of the composition. A humectant provides rheological and/or physical stability and provides various aesthetics for a user. However, for common humectants such as polyols (e.g., glycerin, sorbitol, polyethylene glycol, propylene glycol), the stability of the peroxide active can be negatively affected by large concentrations of the humectant, especially in the presence of polyester. The polyol of the thin layer 14 of the tooth whitening composition can be present in a concentration less than about 40%, preferably between about 0% and about 35%, more preferably between about 1% and about 30%, and most preferably between about 5% and about 15%, by weight of the tooth whitening composition.

In addition, the amount of the humectant/polyol can affect the soluability of the whitening composition in water. The application of a tooth whitening composition to a tooth surface is dynamic throughout the use time of the product. When the tooth whitening composition is applied to the surface of the tooth, the peroxide transfers to the surface of the tooth and into the tooth at a rate that is proportional to the concentration of the whitening active in the composition. The faster the peroxide transfers, the faster the whitening effect occurs. After applying the peroxide active to the tooth surface, the concentration of the peroxide in the finite amount of tooth whitening composition will begin to decrease for several reasons. First, the peroxide that transfers into the tooth lowers the amount of peroxide left in the whitening composition and thus results in a lower concentration. Second, saliva begins to dilute the whitening composition. Third, the peroxide active begins reacting with salivary components (such as bacteria, proteins and enzymes), oral tissues, dental plaque, dental tartar and other oral debris. Thus, the peroxide active is being diluted, transferred and reacted away during the whitening process. When lower amounts of a whitening composition are applied, such as with the present invention, the whitening composition can be diluted to a greater degree with the saliva available in the tissue, on the tissue and in the oral cavity. Thus the water solubility of the tooth whitening composition can affect the shape of the efficacy and tolerability iso-composition loading lines in FIG. 9. Similarly, the peroxide release rate from the whitening composition can also affect the shape of the curves in FIG. 9.

The tooth whitening composition also can include water in a concentration between about 0% and about 92%, preferably between about 50% and about 92%, and more preferably between about 60% and about 90% by weight of the total tooth whitening composition. This concentration of water includes the free water that is added plus that amount that is introduced with other materials.

Figure 11:
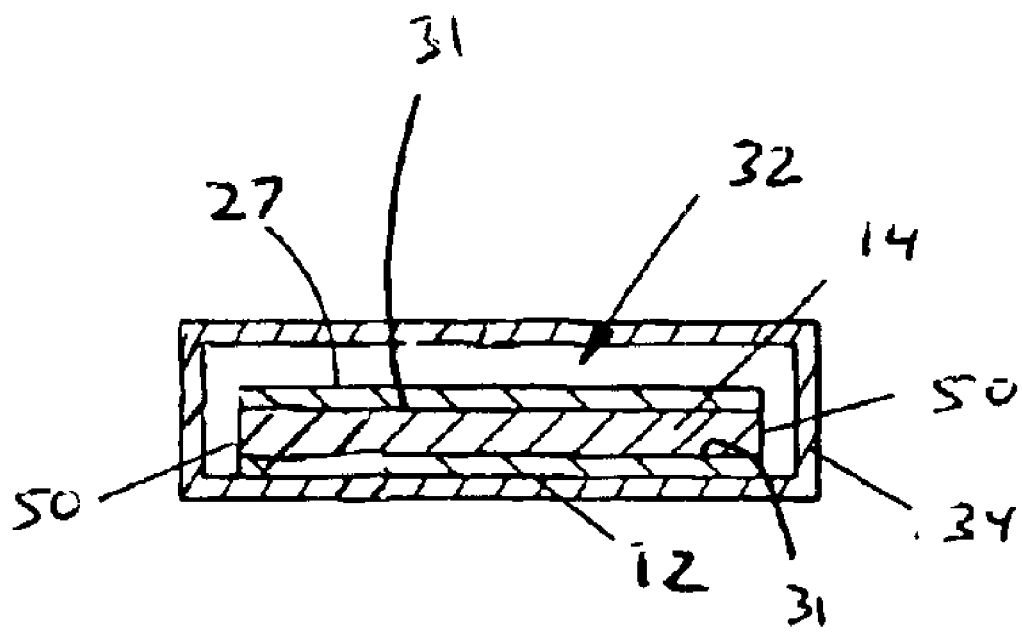
FIG. 11 is a cross sectional side elevational view of a tooth whitening product of the present invention disposed within a package.

Referring to FIGS. 1 to 14, the peroxide stability of the thin layer of the tooth whitening composition can also be improved by appropriate selection of the exposed surface area and volume of the thin layer of the tooth whitening product. As used herein, the term "exposed surface area" is intended to refer to the side surface area of the thin layer of the tooth whitening composition (shown by way of example in FIG. 11 as reference numeral 50) which is directly exposed to head space 32 of a closed package 34 while the volume refers to the volume of the thin layer of the tooth whitening composition. As used herein, the phrase "head space" is intended to refer to the empty volume (i.e., without the tooth whitening product) of the package 34. Both the surface area and volume for this ratio can be lager than the surface area and volume of the tooth whitening composition that is applied to the oral cavity (and therefore different from the surface area value used to calculate the previously discussed peroxide density, peroxide dose, and composition loading values) if there is a sacrificial border or some other peroxide composition disposed within the package which is not applied to the oral cavity. One arrangement having a sacrificial border of tooth whitening composition is shown by way of example in FIGS. 12, 13, and 14. Other arrangements are described in U.S. application Ser. No. 09/675,767, filed Sep. 29, 2000, and now abandoned, the substance of which is incorporated by reference.

Figure 12:
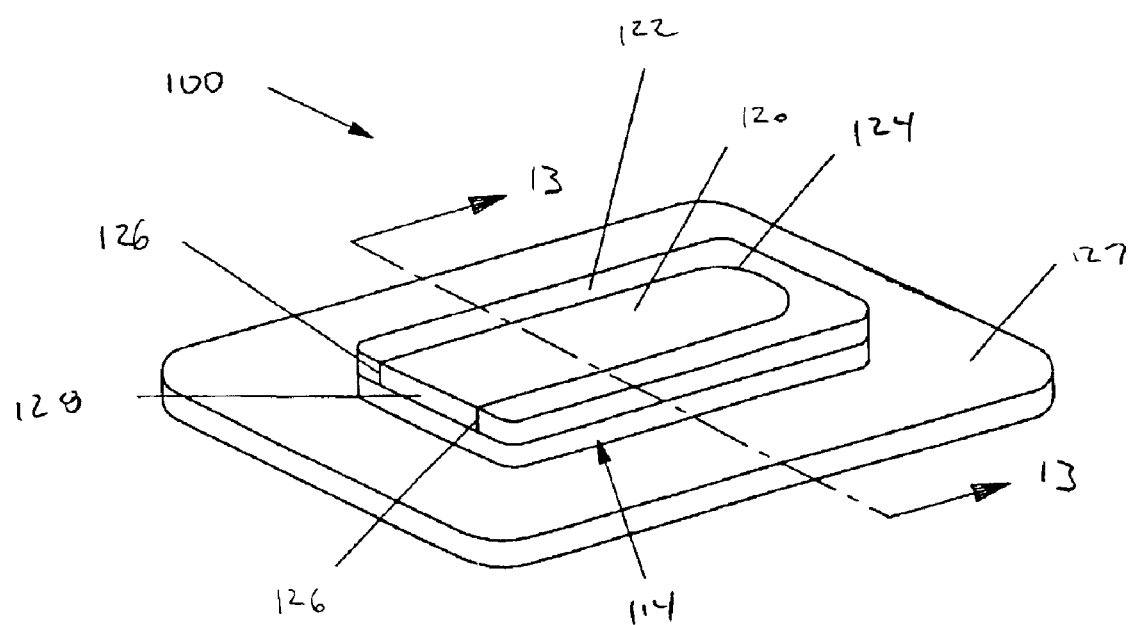
FIG. 12 is a perspective view of another embodiment of the present invention, wherein the tooth whitening product includes a sacrificial border.
Figure 13:
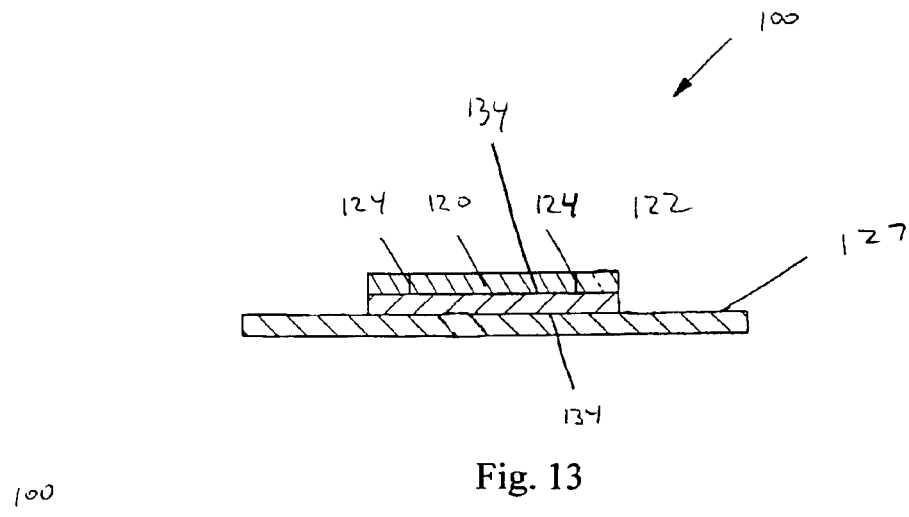
FIG. 13 is a cross-sectional side elevation view of the tooth whitening product of FIG. 12, taken along line 13—13 thereof.
Figure 14:
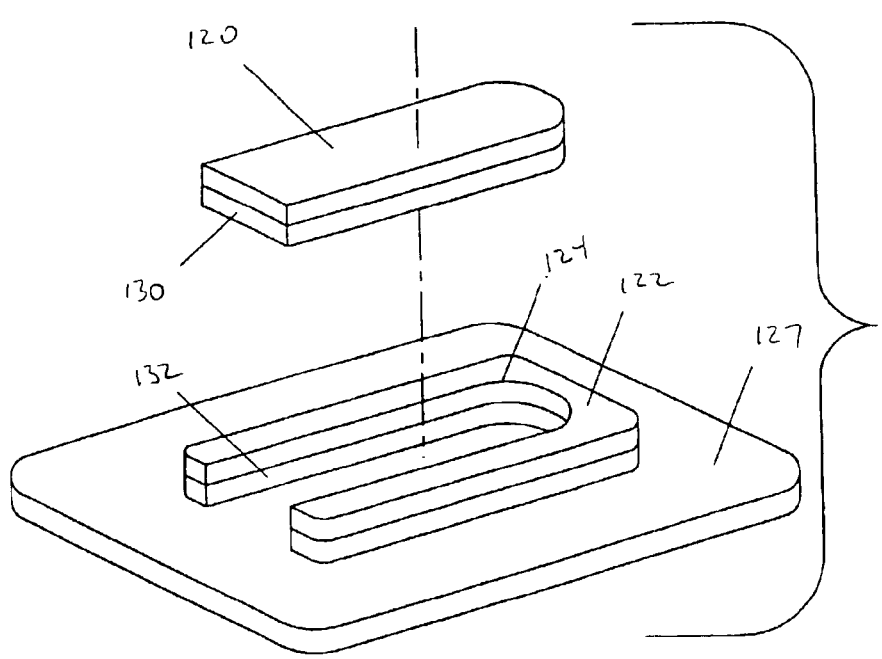
FIG. 14 is a perspective view of the tooth whitening product of FIG. 12, wherein a portion of the strip of material has been removed for application to an oral cavity.

Referring to FIGS. 12, 13, and 14 in greater detail, the tooth whitening product 100 comprises a strip of material having a first section 120 which is applied to the oral cavity and a second section 122 (the sacrificial border) that remains with the release liner 127. The first and second sections 120 and 122 are separated by a slit 124 which preferably passes through the thickness of the strip of material, although a frangible or otherwise partible separation (e.g., a perforated line, a partial slit, etc.) can be employed in place of the slit 124 such that the first and second sections 120 and 122 of the strip of material remain at least partially interconnected until fully separated by a user. The slit 124 can be u-shaped in top plan view, wherein both ends 126 of the slit 124 extend from a common edge 128 of the strip of material. While this arrangement is preferred, it will be appreciated that other slit arrangements can be provided. The first and second sections 120 and 122 of the strip of material overlie first and second sections 130 and 132, respectively, of the thin layer 114 of the tooth whitening composition, as best seen in FIG. 14. In other words, the first section 130 of the tooth whitening composition is substantially coextensive with the first section 120 of the strip of material while the second section 132 of the tooth whitening composition is substantially coextensive with the second section 122 of the of the strip of material. The first and second sections 130 and 132 of the tooth whitening composition are preferably integral with each other until separation during use in order to enhance the peroxide stabilizing effect of the second section 132. However, it is appreciated that partial or full separation between the first and second sections 130 and 132 of the tooth whitening composition might occur during the operation which forms the slit 124. Because the ratio of the exposed surface area to volume of the thin layer of the tooth whitening composition of the tooth whitening product 100 is relatively less than that of a tooth whitening product without the second second sections 122 and 132, it can be a more stable product. In one embodiment, the ratio of the exposed surface area of the entire thin layer of tooth whitening composition (i.e., for all of the tooth whitening composition in the package regardless whether it is or is not applied to the oral cavity) to the volume of that thin layer is less than about 0.12 mm$^{-1}$ and, more preferably, is between about 0.01 mm$^{-1}$ and about 0.18 mm$^{-1}$. Most preferably, the ratio of the exposed surface are of the thin layer 14 to the volume of the thin layer 14 is between about 0.01 mm$^{-1}$ and about 0.15 mm$^{-1}$.

The package 34 can be provided in a variety of shapes and sizes. However, it is desirable that the shape and size of the package 34 closely conform to the shape and size of the tooth whitening product 10. The package can be provided in the form of a pouch, a box, a plastic container, an envelope, a bag, or other suitable package known in the art. A plurality of packages 34 and tooth whitening products 10 can be bundled or otherwise provided as a set so that a sufficient supply of tooth whitening products is available for multi-day use. More preferably, the volume of the headspace 32 of the package 34 is between about 0.1 mm$^3$ and about 30,000 mm$^3$ and, more preferably, is between about 50 mm$^3$ and about 10,000 mm$^3$. The ratio of the volume of the head space 32 to the volume of the thin layer of tooth whitening composition is between 1 and about 500 and, preferably, is between 1 and about 400. More preferably, the ratio of the volume of the head space 32 to the volume of the thin layer of tooth whitening composition is between 1 and about 200 and most preferably is between 1 and about 100. The package 34 should be made of a material that is not translucent, has low or no moisture permeability, and is generally impermeable. The package 34 may be made of one or more materials and may optionally have a liner. For example, a pouch could be made of foil and have a polyethylene lining. Other suitable materials that are not translucent and prevent moisture permeability include plastic, paper, foil, cardboard, polymers, and rubbers. A secondary package (not shown) can also be provided which stores a plurality of the packages 34.

The stability of the peroxide active can also be improved by appropriate selection of the unexposed surface areas of the thin layer of the tooth whitening composition and volume of the thin layer of tooth whitening composition. As used herein, the term "unexposed surface area" is intended to refer to the surface areas of the thin layer of tooth whitening composition which are not directly exposed to the headspace of a package, such as the surface areas 134 which are disposed adjacent the strip of material and the release liner 127. The surface area and volume for this ratio can be larger than the surface area and volume that is applied to the oral cavity (and therefore different from the surface area value used to calculate the previously discussed peroxide density, peroxide dose, and composition loading values) if there is a sacrificial border or some other peroxide composition disposed within the package which is not applied to the oral cavity. The ratio of the unexposed surface area of the thin layer of tooth whitening composition to the volume of the thin layer of the tooth whitening composition is less than about 1500 cm$^{-1}$ and, more preferably, is between about 5 cm$^{-1}$ and about 500 cm$^{-1}$. Most preferably, the ratio of the unexposed surface of the thin layer of the tooth whitening composition to the volume of the thin layer of the tooth whitening composition is between about 10 cm$^{-1}$ and about 110 cm$^{-1}$.

In general, a tooth whitening product having one or more of a polyol concentration of less than about 40%, a ratio of the exposed surface area of the thin layer to the volume of the thin layer of less than about 0.2 mm$^{-1}$, a ratio of the unexposed surface area of the thin layer to the volume of the thin layer of less than about 1500 cm$^{-1}$, or the material forming the surfaces of the strip of material 12 and the release liner 27 which is in contact with the tooth whitening composition are polyolefins can have between about 10% and about 70% of the original concentration of the peroxide active present at twelve months after its manufacture. In another embodiment, such a tooth whitening product may have between about 10% and about 50% of the original concentration of the peroxide active present at twelve months after manufacture.

It has been found that the largest increases in stability of the peroxide active are from decreasing the concentration of the polyol or decreasing the value of the ratio of the exposed surface area of the thin layer 14 to the volume of the thin layer. Lesser increases in the stability of the peroxide active are achieved by the release liner and strip of material material and decreasing the value of the ratio of the unexposed surface area of the thin layer to the volume of the thin layer.

Figure 15:
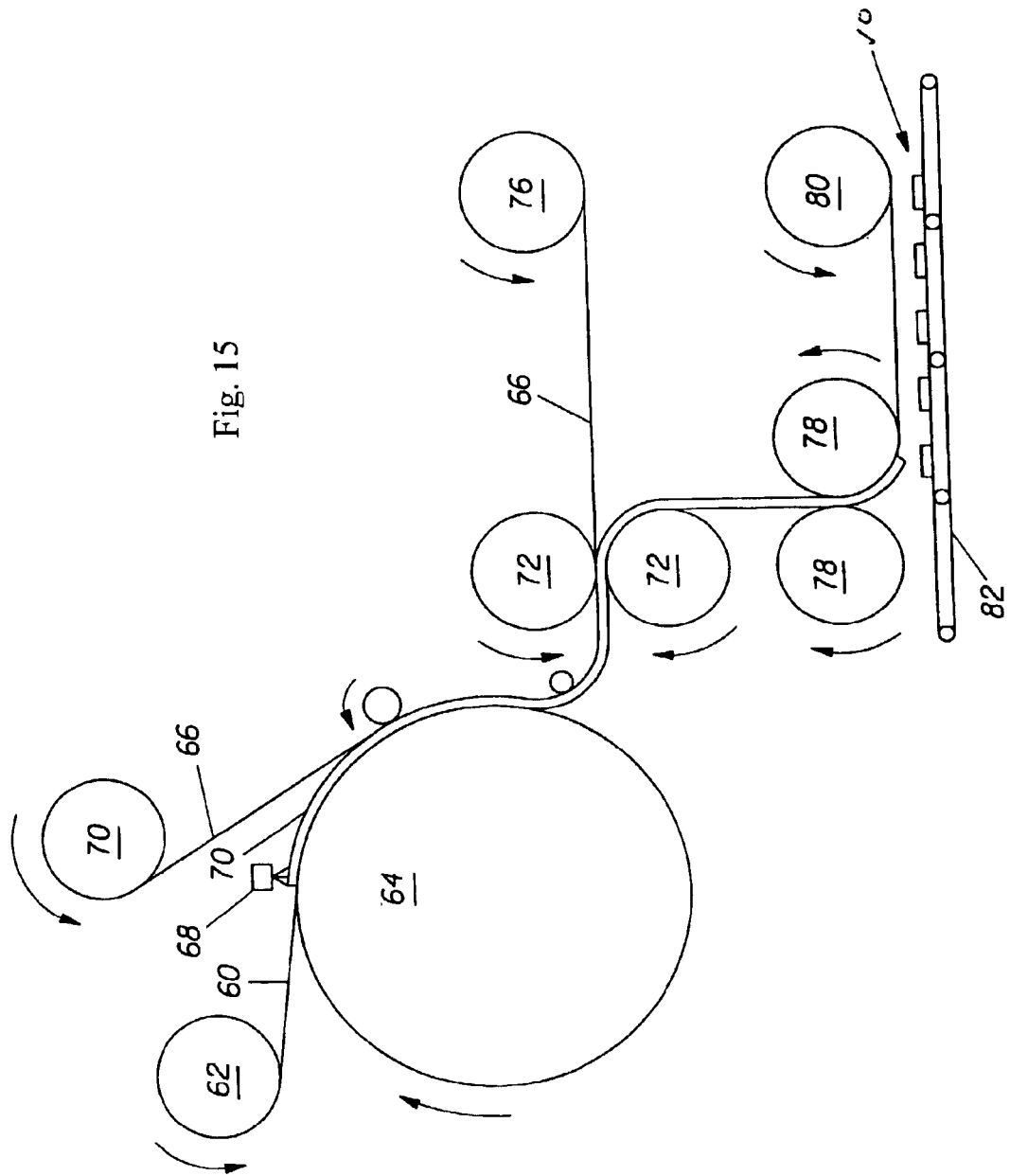
FIG. 15 is a schematic illustration of a manufacturing line for making the tooth whitening product of FIG. 1.

Referring to FIG. 15, a preferred method for forming tooth whitening products of the present invention will now be described. A sheet 60 of the release liner 27 is unrolled from the roller 62 and is fed over drum 64. The sheet 60 of the release liner 27 (as well as sheet 66 of the strip of material 12) may be formed by any one of several film making processes known in the art (e.g., a blown process or a cast process). Processes, such as extrusion and other processes that do not affect the flexural rigidity of the strip of material might also be used. A nozzle 68 applies a thin layer 70 of the tooth whitening composition onto the sheet 60 of the release liner 27. The appropriate thickness of the thin layer can be achieved by proper selection and design of the nozzle 68 as well as design and selection of the drum bearings and other elements of the manufacturing system that might affect deposition of the thin layer on the sheet 60. The sheet 66 of the strip of material 12 is unrolled from the roller 70 and lightly pressed onto the thin layer 70 of the tooth whitening composition, thereby forming a three layer laminate. The laminate is fed to the rollers 72 which create the slit 40 as well as cut through the sheet 66 of the strip of material 12 and the thin layer 70 of the tooth whitening substance 12 to define the outer edges 74 (FIG. 5) of the second sections 38 and 48 thereof. After the cutting and slitting operation at rollers 72, the excess sheet 66 of the strip of material 12 is taken up by the roller 76, thereby leaving the first and second sections of the strip of material 12 and the tooth whitening composition on the sheet 60 of the release liner 27. The rollers 78 cut the release liner 27 to form individual tooth whitening products 10. The excess release liner 27 is taken up by the roller 80 while the tooth whitening products 10 are collected by the conveyor 82, after which the tooth whitening products can be inserted into a package to form a packaged tooth whitening product. As will be appreciated, these steps can be rearranged, deleted, and other steps added as is known in the art.

In general, after manufacture, the tooth whitening product 10 is stored in the package (and/or in a secondary package or packages) at least about twelve months between about 20° C. and about 45° C. and substantially in the absence of light (if the package is not opaque), although it is contemplated that at least a portion of this storage time (typically two to four months) can occur under refrigeration. More preferably, the tooth whitening product is stored at about room temperature (e.g., about 25° C.) in the absence of light (if the package is not opaque). After storage, the package can be opened by a user and the tooth whitening product is removed from the package. Following storage and after application of the tooth whitening composition to the teeth using the strip of material 12, at least a portion of a tooth (and more desirably an entire tooth) will be whitened.

METHOD FOR DETERMINING WHITENING EFFICACY

Tooth color can be measured by using a digital camera having a 4×50 motorized zoom lens equipped with a polarizer filter, such as camera model no. HC-1000 manufactured by Fuji Film Corp. of Japan. The lighting system can be provided by Dedo lights equipped with 150 watt, 24V bulbs positioned 35 cm apart and aimed at a 45 degree angle such that the light paths intersect 114 cm in front of each light. Each light has a polarizing filter and a cutoff filter.

At the intersection of the light paths, a fixed chin rest can be mounted for reproducible repositioning in the light field. The HC1000 camera is placed between the two lights and focused on the chin rest. Prior to beginning the measurement of tooth color, color standards are imaged to establish calibration set-points. A white standard is imaged first. The white balance of the camera is adjusted such that the RGB values are 250, 250 and 250, respectively. Next, the lens cover is placed on the lens to eliminate all light and the black balance is set using the auto black feature of the camera. Lastly, a macbeth color chart is imaged to get standard RGB values of the color chips.

For baseline tooth color, subjects brush with water to remove any debris from their teeth. Each subject then uses lip retractors to pull the cheeks back and allow the facial surfaces of their teeth to be illuminated. Each subject is instructed to bite their teeth together such that the incisal edges of the maxillary incisors contact the incisal edges of the mandibular incisors. The subjects are then positioned in the center of the camera view and the tooth images are captured. After all subjects are imaged, the images can be processed using an image analysis software, such as Optimas manufactured by Media Cybernetics, Inc. of Silver Spring, Md. The central four incisors are isolated and the average RGB values of the teeth are extracted.

After the subjects have used a whitening product but prior to capturing subject's tooth images, the system is set to the baseline configuration and calibrated as previously discussed. After calibration, each subject is imaged a second time using the same procedure as before. The images are processed using the image analysis software to obtain the average RGB values of the central four maxillary incisors. The RGB values of all of the images are then mapped into CIE L*a*b* color space using the RGB values and the L*a*b* values of the color chips on the color standard. The L*a*b* values of the color chips on the color standard can be measured using a Photo Research SpectraScan PR650 and the same lighting conditions described for capturing digital images of the facial dentition. Each chip is individually measured for L*a*b* after calibration according to the manufacturers instructions. The RGB values are then transformed into L*a*b* values using the following transformation equations:

$$L^*=0.104^*R+0.183^*G+0.00847^*B+20.12$$

$$a^*=0.319^*R-0.468^*G+0.138^*B+3.82$$

$$b^*=0.176^*R+0.262^*G-0.425^*B-1.78$$

These equations are generally valid transformations in the area of tooth color ($60<L^*<95$, $0<a<14$, $6<b<25$). The data from each subject's set of images is then used to calculate product whitening performance in terms of changes in L*, a* and b*—a standard method used for assessing whitening benefits. Changes in L* (luminance) is defined as $\Delta L^*=L_{day\ 14}-L_{baseline}$. A positive change indicates improvement in brightness. Changes in a* (red-green balance) is defined as $\Delta a^*=a_{14}-a_{baseline}$. A negative change indicates teeth which are less red. Changes in b* (yellow-blue balance) is defined as $\Delta b^*=b^*_{day\ 14}-b^*_{baseline}$. A negative change indicates teeth are becoming less yellow. An overall color change is calculated by the equation $\Delta E=(\Delta L^2+\Delta a^{*2}+\Delta b^{*2})^{1/2}$.

After using the whitening products, color changes in CIE Lab color space can be calculated for each subject based on the equations given. The average color change for each group of subjects is determined by the average in the individual changes in the CIE color parameters. This can produce an average $\Delta L$, $\Delta a$ and $\Delta b$ for a whitening product.

METHOD FOR DETERMINING PERCENTAGES AND CONCENTRATIONS OF PEROXIDE ACTIVES

Peroxide concentrations can be measured using the Iodometric titration method (*"Hydrogen Peroxide"*, Walter C. Schumb, Reinhold Publishing, copyright 1955). The Iodometric titration method is a standard method known in the art for measuring peroxide concentration. In general, the method is performed by weighing the strip of material and composition containing the peroxide active, dissolving the composition in IM sulfuric acid, and reacting the peroxide with an excess of 10% potassium iodide aqueous solution (granular reagent available from J.T. Baker cat no. 3162-01, CAS no. 7681-11-0) in the presence of a few drops of 1% ammonium molybdate (VWR cat no. VW3627-1,). This is then titrated with a 0.025N concentration of sodium thiosulfate (VWR cat. No. VW3127-1) to a clear endpoint using a starch indicator. The 1% starch indicator (VWR cat no. VW3368-1) is added when the titration solution is a pale yellow. The strip of material is weighed upon completion of the titration and the composition weight is determined by difference from the starting weight of the device plus the weight of the composition. The peroxide concentration in the composition can then be calculated.

If the peroxide concentration is measured after a period of storage of the tooth whitening product and the storage period is long, the concentration of the peroxide active can alternatively be determined by measuring the concentration as described above after at least one hundred and twenty days and then extrapolating for the remainder of the period using first order kinetics, as is known in the art. The above-described method can be performed just after manufacture of a peroxide product and at the end of the specified storage period in order to determine the absolute peroxide concentrations as well as the percentage of the original concentration remaining, as is known in the art.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A tooth whitening product, comprising:
   a strip of material sized to cover the front surface of one or more teeth and soft tissue adjacent the front surface of the one or more teeth;
   a layer of a tooth whitening composition disposed on said strip of material, wherein said whitening composition comprises a peroxide active having a concentration greater than about 7.5% by weight of said tooth whitening composition; and
   wherein said tooth whitening composition has a peroxide density less than about 1.3 mg/cm$^2$.

2. The tooth whitening product of claim 1, wherein said peroxide active has a concentration between about 8% and about 40%.

3. The tooth whitening product of claim 1, wherein said peroxide active has a concentration between about 10% and about 20%.

4. The tooth whitening product of claim 1, wherein said peroxide density is between about 0.01 mg/cm$^2$ and about 1.3 mg/cm$^2$.

5. The tooth whitening product of claim 1, wherein said peroxide density is between about 0.5 mg/cm$^2$ and about 1.3 mg/cm$^2$.

6. The tooth whitening product of claim 1, wherein said tooth whitening composition further comprises water.

7. The tooth whitening product of claim 6, wherein the amount of said water is up to about 92% by weight of said both whitening composition.

8. The tooth whitening product of claim 6, wherein the amount of said water is between about 60% and about 90% by weight of said tooth whitening composition.

9. The tooth whitening product of claim 1, wherein said tooth whitening composition further comprises a gelling agent.

10. The tooth whitening product of claim 9, wherein the amount of said gelling agent is between about 1% and about 10% by weight of said tooth whitening composition.

11. The tooth whitening product of claim 9, wherein the amount of said gelling agent is between about 3% and about 6% by weight of said tooth whitening composition.

12. The tooth whitening product of claim 1, wherein the thickness of said layer is less than about 0.3 mm.

13. The tooth whitening product of claim 1, wherein the thickness of said layer is between about 0.008 mm and about 0.1 mm.

14. A packaged tooth whitening product, comprising:
    a package having a headspace;
    a strip of material sized to cover the front surface of one or more teeth and soft tissue adjacent said front surface, wherein said strip of material is disposed within said package;
    a layer of a tooth whitening composition disposed on said strip of material, wherein said tooth whitening composition comprises a peroxide active having a concentration between about 7.5% and about 40% by weight of said tooth whitening composition; and
    wherein said tooth whitening composition has a peroxide density between about 0.01 mg/cm$^2$ and about 1.3 mg/cm$^2$.

15. The packaged tooth whitening product of claim 14, wherein said tooth whitening composition has a composition loading between about 0.0005 gm/cm$^2$ and about 0.03 gm/cm$^2$.

16. The packaged tooth whitening product of claim 14, wherein said tooth whitening composition has a composition loading between about 0.01 gm/cm$^2$ and about 0.02 gm/cm$^2$.

17. The packaged tooth whitening product of claim 14, wherein said peroxide active has a concentration between about 10% and about 20%.

18. The packaged tooth whitening product of claim 14, wherein said layer has a thickness less than about 0.1 mm.

19. The packaged tooth whitening product of claim 14, wherein said tooth whitening composition further comprises a gelling agent.

20. The packaged tooth whitening product of claim 19, wherein the amount of said gelling agent is between about 2% and about 8% by weight of said tooth whitening composition.

* * * * *